United States Patent [19]

May et al.

[11] Patent Number: 5,358,711
[45] Date of Patent: Oct. 25, 1994

[54] STIMULATION OF STEM CELL GROWTH BY THE BRYOSTATINS

[75] Inventors: W. Stratford May, Baltimore, Md.; Lyle L. Sensenbrenner, Grosse Pointe Park, Mich.

[73] Assignee: Johns Hopkins University, Baltimore, Md.

[21] Appl. No.: 118,694

[22] Filed: Sep. 10, 1993

Related U.S. Application Data

[63] Continuation of Ser. No. 987,999, Dec. 9, 1992, abandoned, which is a continuation of Ser. No. 123,736, Nov. 23, 1987, abandoned.

[51] Int. Cl.⁵ .................. A61K 35/14; A61K 31/365; A61K 35/28; C12N 5/08
[52] U.S. Cl. .............................. 424/93.7; 435/240.1; 435/240.2; 435/240.21; 435/2; 514/449; 514/885; 424/93.71; 424/93.73
[58] Field of Search ............ 435/240.2, 240.1, 240.21, 435/240.3, 2; 514/449, 885; 604/4; 424/93 U, 93 V, 93 AA

[56] References Cited

U.S. PATENT DOCUMENTS 4,560,774 12/1985 Pettit et al. .
4,611,066 9/1986 Pettit et al. .

OTHER PUBLICATIONS

Junqueira, et al., "The Life Cycle of Blood Cells", Basic Histology, pp. 244–260, Junqueira, et al editors, 1971.
McLeod, et al., Blood (1974) 44:517–534.
Fibach, et al, "Tumor Promoters Enhance Myeloid and Erythroid Colony Formation By Normal Mouse Hemopoietic Cells", Proc. Natl. Acad. Sci. USA (1980) 77:4152–4155.
Stuart, et al., "Tumor-Promoting Phorbol Esters Stimulate Hematopoietic Colony Formation In Vitro", Science (1980) 208:402–406.
Pettit, et al., "The Structure of Bryostatin 2 From the Marine Bryozoan *Bugula Neritina*", Journal of Natural Products (1983) 46: 528–531.
Ozawa, et al., "Effects of 12-O-Tetradecanoylphorbol 13-Acetate on the Proliferation and Differentiation of Normal and Leukemic Myeloid Progenitor Cells", Cancer Research (1983) 43:2306–2310.
Quesenberry, in Williams, et al., eds., "Hematology," 3rd ed. McGraw-Hill, 1983, p. 136.
Aye, et al., "Opposing Effects of 12-O-Tetradecanoylphorbol 13-Acetate on Human Myeloid and Lymphoid Cell Proliferation", J. Cell. Phys. (1983) 114:209–214.
Sullivan, et al., "The Effects of Tumor-Promoting Phorbol Esters on Human Granulopoiesis in Vitro", Blood (1984) 64:526–533.
Pettit, et al., "Structure of Bryostatin 4. An Important Antineoplastic Constituent of Geographically Diverse *Bugula neritina* (Bryozoa)", J. Am. Chem. Soc. (1984) 106:6768–6771.
Paul, ed., "Fundamental Immunology", Raven Press, New York (1984) pp. 699–703.
Park, "Preferential Growth Inhibition of Human Leukemic Versus Normal Myeloid Colony-Forming Cells by 12-O-Tetradecanoylphorbol-13-acetate", Exp. Hematol. (1984) 12:285–290.
Smith, et al, "Bryostatins: Potent, New Mitogens That Mimic Phorbal Ester Tumor Promoters", Biochem. & Biophys. Res. Comm. (1985) 1332:939–945.
Wong, et al., "Human GM-CSF: Molecular Cloning of the Complementary DNA and Purification of the Natural and Recombinant Proteins", Science (1985) 228:810–815.

(List continued on next page.)

*Primary Examiner*—George C. Elliott
*Attorney, Agent, or Firm*—Banner, Birch, McKie & Beckett

[57] ABSTRACT

In vivo and in vitro methods are taught for stimulating the differentiation of stem cells using certain bryostatins. Stem cells can be induced to form granulocytes, macrophages and erythrocytes. In addition, the cytotoxicity of mature neutrophils can be activated. These methods may substitute for those requiring human colony stimulating factors.

28 Claims, 5 Drawing Sheets

OTHER PUBLICATIONS

Pettit, et al., "Antineoplastic Agents 100; The Marine Bryozoan *Amathia Convoluta*", Tetrahedron (1985) 41:985–994.

Berkow, et al., "Bryostatin, A Non-Phorbol Macrocyclic Lactone, Activates Intact Human Polymorphonuclear Leukocytes and Binds to the Phorbol Ester Receptor", Biochemical And Biophysical Res. Communications (1985) 131:1109–1116.

Berkow, et al., "Bryostatin Activates Human Neutrophils By Binding To The Phorbol Receptor", Clin. Res. (1985) 33:335A.

Metcalf, et al., "Biologic Properties In Vitro of a Recombinant Human Granulocyte-Macrophage Colony-Stimulating Factor", Blood (1986) 67:34–45.

Kraft, et al., "Bryostatin, an Activator of the Calcium Phospholipid-Dependent Protein Kinase, Blocks Phorbol Ester-Induced Differentiation of Human Pro-Myelocytic Leukemia Cells HL-60", Proc. Natl Acad. Sci. USA (1986) 83:1334–1338.

May, et al., "Antineoplastic Bryostatins Are Multipotential Stimulators of Human Hematopoietic Progenitor Cells", Proc., Natl. Acad. Sci. USA (1987) 84:8483–8487.

Dell'Aquila, et al., "Inhibition by Bryostatin 1 of the Phorbol Ester-Induced Blockage of Differentiation In Hexamethylene Bisacetamide-treated Friend Erythroleukemia Cells", Cancer Res. (1987) 47:6006–6009.

Hennings, et al., "Bryostatin 1, an Activator of Protein Kinase C, Inhibits Tumor Promotion by Phorbol Esters in SENCAR Mouse Skin", Carcinogenesis (1987), 8:1343–1346.

Ramsdell, et al., "Three Activators of Protein Kinase C, Bryostatins, Dioleins, and Phorbol Esters, Show Differing Specificities of Action on $GH_4$ Pituitary Cells", J. Biol. Chem. (1986) 2561:17073–17080.

Fields, et al., "Phosphorylation of Lamin B at the Nuclear Membrane by Activated Protein Kinase C", J. Biol. Chem. (1988) 63:8252–8260.

Jandl, "Blood: Textbook Of Hematology", Little, Brown and Co., Boston/Toronto, 1987, p. 1.

Leonard, et al., "Regulation of Hematopoiesis IV: The Role of Interleukin-3 and Bryostatin 1 in the Growth of Erythropoietic Progenitors from Normal and Anemic $W/W^v$ Mice", Blood (1988) 72:1492–1496.

May, et al., Abst. 466, Blood (1986) 68:147a.

May, et al., "Bryostatin Activates Protein Kinase C And Is A Multi-Potential Stimulator of Human Hematopoietic Progenitors", ISEH Abst. (1987).

Gebbia, et al., "Bryostatin-1 Stimulates Multipotential Murine Hematopoietic Stem Cells In Vivo", Blood (1987) 70:153a.

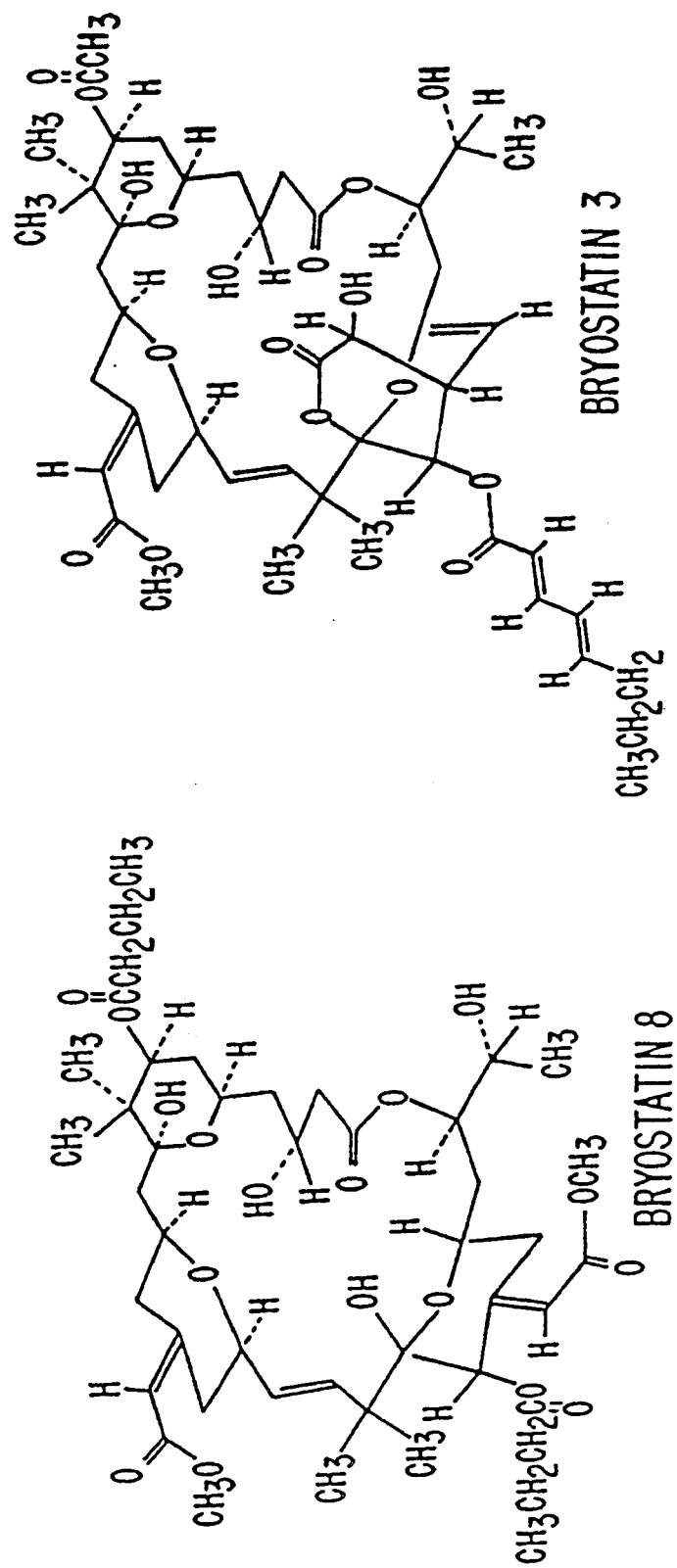

STIMULATION OF STEM CELL GROWTH BY THE BRYOSTATINS

The work reported here was partially supported by grants from National Institutes of Health. The U.S. Government may retain certain rights in this invention.

This application is a continuation of application Ser. No. 07/987,999, filed Dec. 9, 1992, now abandoned, which is in turn a continuation of application Ser. No. 07/123/736 filed Nov. 23, 1987, now abandoned.

TECHNICAL FIELD OF THE INVENTION

This invention relates to chemical agents having stimulatory effects on growth and activity of hematopoietic cells. More particularly, the invention relates to the use of bryostatins to stimulate growth and activity of hematopoietic cells.

BACKGROUND OF THE INVENTION

The bryostatins are a family of macrocyclic lactones which have been isolated from specimens of marine bryozoans. The sea-mat *Bugula neritina* has been the source of many of the bryostatins. Others have been isolated from the marine animal *Amathia convoluta*, also a member of the phylum Bryozoa.

All of the bryostatins are derived from the bryopyran ring system (Petitt et al, Journal of Natural Products, Vol. 46, pp. 528–531, 1983) and all are reported to have antineoplastic activity aganist a single murine leukemia cell line, the P388 lymphocytic leukemia line. The bryostatins substantially inhibit P388 cell growth in vitro, and also are able to increase the life span of mice injected with P388 lymophocytic leukemia cells. Bryostatins 1–8 are described in Pettit U.S. Pat. No. 4,560,774 and U.S. Pat. No. 4,611,066.

There are many health conditions which result in a deficiency of hematopoietic cells. For example, a problem often arises in the treatment of cancers with antineoplastic agents; these agents can have an inhibitory effect on normal bone marrow progenitor cells (stem cells). In addition, there are many diseases in which neutropenias result, such as acquired immune deficiency syndrome (AIDS).

There are also many conditions in which erythroid cells are insufficient to support normal activity, such as congential anemias, and Fanconi's anemia. Diseases such as rheumatoid arthritis and lupus erythematosus, often result in depletion of certain populations of blood cells. Therefore there is a continuing need in the art for agents which are safe to administer and which stimulate the development of various types of hematopoietic cells.

SUMMARY OF THE INVENTION

It is an object of the present invention to provide a method of stimulating stem cells to proliferate and to differentiate to form granulocytes, macrophages, or erythrocytes in vitro.

It is another object of the invention to provide a method of stimulating stem cell proliferation and differentation in a mammal.

It is an additional object of the present invention to provide a method of stimulating stem cell proliferation and differentation in tumor-bearing mammals.

It is yet another object of the present invention to provide a method of activating neutrophils and other immune regulatory cells, e.g., T lymphocytes and macrophages, in vitro.

It is still another object of the present invention to provide a method of activating neutrophils and other immune regulatory cells in a mammal.

These and other objects of the invention are provided in the detailed description below. In one embodiment a method of stimulating stem cells to form granulocytes, macrophages, erythrocytes, is provided comprising: obtaining a cell preparation containing stem cells and incubating the cell preparation in vitro with an effective amount of a bryostatin having an acylated C2O carbon to stimulate formation of granulocytes, macrophages or erythrocytes, whereby said formation is stimulated.

In yet another embodiment of the present invention a method is provided for stimulating stem cell differentiation to form granulocytes, eosinophils, basophils, platelets, macrophages or erythrocytes in a mammal, comprising: administering a bryostatin having an acylated C2O carbon to the mammal in an amount effective to stimulate formation of granulocytes, eosinophils, basophils, platelets, macrophages or erythrocytes, whereby said formation is stimulated.

In yet another embodiment of the present invention, a method is provided of activating neutrophils and other immune regulatory cells, comprising: obtaining a neutrophil or other immune regulatory cell preparation and incubating the cell preparation in vitro with an amount of a bryostatin having an acylated C2O carbon effective to activate the cytotoxicity of the neutrophils and other immune regulatory cells, whereby said cytotoxicity is activated.

In another embodiment of the present invention, a method is provided of activating neutrophils and other immune regulatory cells in a mammal, comprising: administering a bryostatin having an acylated C2 O carbon to the mammal to activate neutrophil and other immunergulatory cell cytotoxicity, whereby said cytotoxicity is activated.

The methods of the present invention provide means of stimulating stem cell growth with molecules which show low levels of toxicity. The bryostatin molecules, which are based on a 37 carbon macrocyclic lactone structure, can substitute for naturally occurring colony stimulating factors for some purposes. However, in other ways the activity of the bryostatins appears to differ from that of naturally occurring colony stimulating factors. Thus the bryostatins, but not colony stimulating factors, stimulate stem cell differentiation without also stimulating growth of neoplastic cells.

DETAILED DESCRIPTION

It is a finding of the present inventors that certain bryostatins, are able to effect hematopoiesis. The morphological analysis of the colonies which are stimulated by bryostatins reveals that primarily mixed granulocyte-macrophage colonies and pure granulocyte colonies are formed from light-density, adherence-depleted, normal human bone marrow cells.

The bryostatins themselves can be obtained by extraction and purification from the marine bryozoan *Bugula neritina*. Description of the extraction and purification techniques can be found in Pettit et al, Journal of American Chemical Society, Vol. 104, pp. 6846, 6848, 1982, and Pettit et al, Journal of Natural Products, Vol. 46, pp. 528–531, 1983. Some of these compounds are also described in U.S. Pat. No. 4,560,774 and U.S. Pat. No. 4,611,066. Generally, the bryostatins can be isolated and purified by solvent extraction, partition chromatography, silica gel chromatography, liquid-liquid distribution in a Craig apparatus, absorption on resins and crystallization from solvents. Isolation and purification methods can be monitored at each step by performing in vitro or in vivo anti-tumor tests, or by looking for activation of neutrophils or stimulation of formation of granulocytes, macrophages or erythrocytes from stem cells.

Figure 1A:
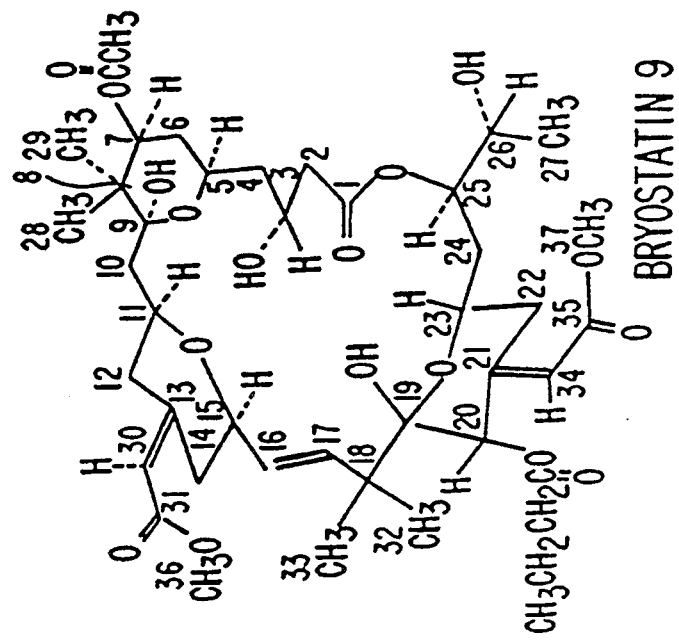
FIG. 1 depicts the chemical structures of the bryostatins. Panel A: bryostatin 1; panel B: bryostatin 9; panel C: bryostatin 8; panel D: bryostatin 3; panel E: bryostatin 13.
Figure 1B:
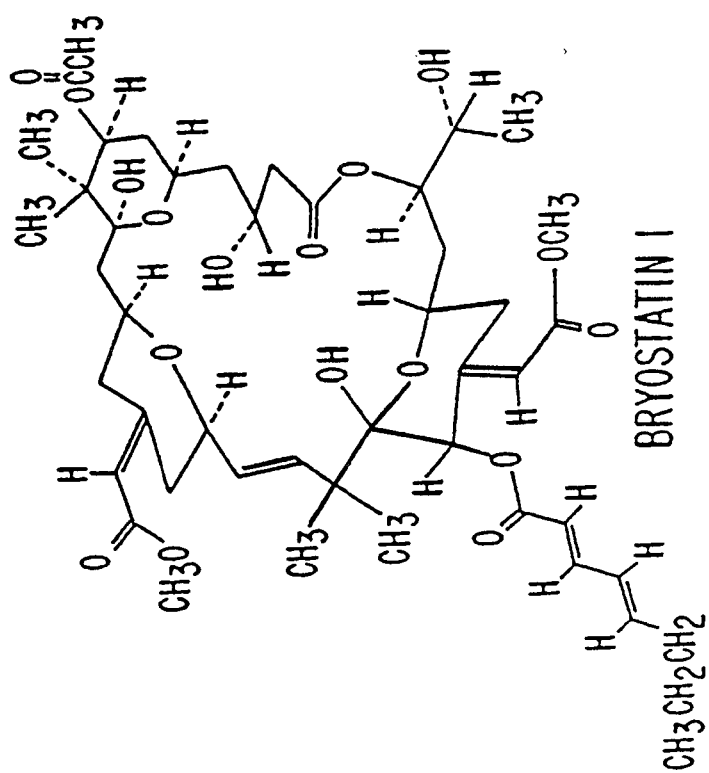
Figure 1E:
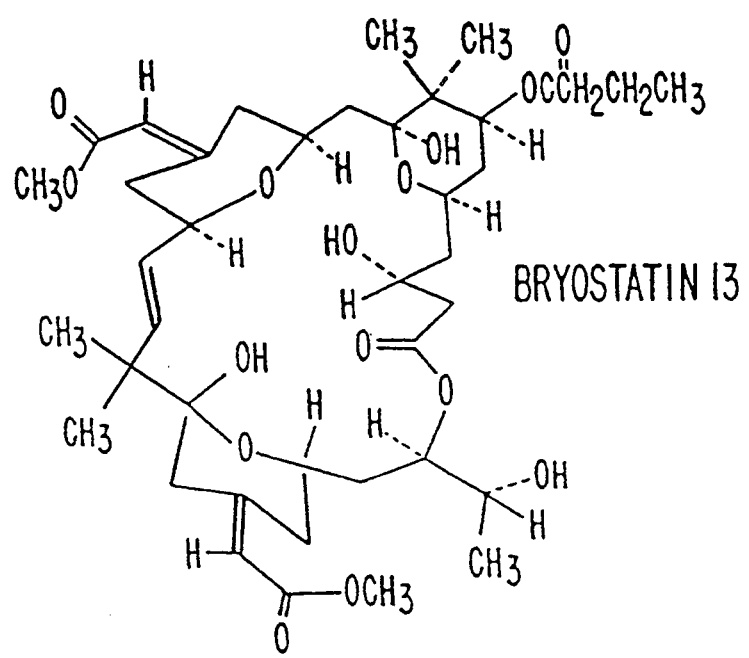

Not all bryostatins have the same amount of activity. For example, in the granulocyte-macrophage colony growth assay, bryostatin 1 has more activity than 3 which had more activity than 8 which had more activity than 9. Bryostatin 13 was totally inactive in this assay. When the structure-activity relationships of the bryostatins are examined, the results indicate that both the hematopoietic colony stimulating activity as well as the functional activation of neutrophils may be dependent upon acylation of carbon 20 (see FIG. 1). Thus, when the short-chain, saturated butyric acid was substituted in bryostatin 1 at carbon 20, the resulting bryostatin 9 was a much less potent stimulator of granulocyte-macrophage colony forming units (GM-CFU). This decrease in activity was restored when a substitution involving a longer acyl group at carbon 7 was made, as in bryostatin 8. However, when the acyl substitution on carbon 20 was completely removed, as in bryostatin 13, both colony stimulating activity and neutrophil activation was lost. Furthermore, the loss of activity does not result from a toxic effect of bryostatin 13, since when bryostatin 1 was mixed with bryostatin 13, the expected degree of granulocyte-macrophage colony formation obtained with broystatin 1 alone was observed. Bryostatin 13, which is inactive in the hematopoietic stimulating activities reported herein, is reported by others to retain potent antineoplastic activity. (See Pettit, et al, Journal of Organic Chemistry, (1957).)

Bryostatins 1, 3, 8 and 9 (see FIG. 1) have been found to mediate a dose dependent stimulation of granulocyte and macrophage colony forming units (CFU-GM). The maximum effective concentration is between about 1 and 100 nM. Bryostatins 1 and 8 are the most potent of the four active congeners tested. They show colony stimulating activity at concentrations as low as 0.01 nM. Bryostatin 3 is less potent than bryostatins 1 and 8 having a maximal response between about 10 and 100 nM. Bryostatin 9 is a weaker stimulator of normal colony growth, and bryostatin 13 is completely inactive. Thus the hierarchy of bryostatin activity is that bryostatin 1 is most active and bryostatins 3, 8 and 9 are increasingly less active, and bryostatin 13 is totally inactive.

Cell preparations containing stem cells can be obtained from bone marrow or from peripheral blood cells. These can be purified using techniques known in the art, such as density gradient centrifugation, to remove red blood cells. Alternatively, stem cells can be purified using antibodies which are specific for stem cell antigens. (See, Civine et al, Journal of Immunology, Vol. 133, p. 157, 1984).

Amounts of bryostatin which are effective for stimulating hematopoiesis or neutrophil and other immune regulatory cell activation, can be determined using any of the assays known in the art. For example, early and late erythrocyte progenitors can be enumerated using the plasma clot method described in McLeod et al, Blood, Vol. 44, p. 517, 1974. Stimulation of such erythrocyte progenitors requires the presence of erythropoietin. For bryostatin 1, optimum stimulation of erythrocytes was seen at about $10^{-12}M$ to about $10^{-10}M$.

For determining effective concentrations of bryostatins for granulocyte and macrophage colony formation, light density, adherence-depleted human bone marrow cells can be obtained. The cells can be suspended in a suitable medium, such as supplemented McCoy's 5A medium containing 0.3% agar and plated in 35 mm petri dishes as described in Pike et al, Journal of Cell Physiology, Vol. 76, pp. 77–83, 1970. For the bryostatins which have been tested and found to be effective, i.e., 1, 3, 8 and 9, maximum stimulatory concentrations are between about $10^{-7}M$ and $10^{-10}M$.

To determine the effective amount of bryostatin for neutrophil activation, normal human peripheral blood neutrophil cells can be purified on a density gradient such as a Ficoll gradient. Other immune regulatory cells, such as T-lymphocytes and macrophages can be isolated by standard and known techniques. The neutrophils can be suspended in Dulbecco's phosphate-buffered saline supplemented with calcium and magnesium. One way to monitor neutrophil activation is to observe chemiluminescence. The neutrophils can be incubated for about fifteen minutes with the bryostatin. Then luminol (5-amino-2,3-dihydro-1,4-phthalazinedione) can be added to a concentration of about 10 $\mu$M. Chemiluminescence can be measured in a luminometer as described in Allen et al, Biochemistry and Biophysics Research Communications, Vol. 69, pp. 245–522, 1976.

Alternatively, neutrophil activation can be assayed using a cytoxicity assay. Purified neutrophils can be incubated at a density of about $3 \times 10^6$ cells per ml with various concentrations of bryostatin. The cells can be washed and added to radiolabelled target cells. K562 tumor cells and $^{51}$Cr-label can be used to measure cytoxicity. The target cells are preincubated with the radiolabelled substance to effect uptake of the radiolabel. The target cells can be mixed with the netrophils at various effector to target cell ratios, such as between about 50:1 and 5:1. Release of label from the target cells can be measured, either by assaying in the superrnatant or the cells after centrifugation. Of course, other methods known in the art, such as using other assays of immune regulatory cell cytotoxicity can be used. Bryostatin 1 has activity toward neutrophils at about $10^{-10}$ to $10^{-7}M$, with a maximum activation effect on neutrophil cytotoxicity of K562 target cells at a concentration of about $10^{-7}M$.

It may be advantageous to treat either cells or mammals concommitantly with bryostatin and a chemotherapeutic agent or ionizing radiation. For example, it may be desirable to purge a cell suspension of all malignant cells while sustaining the viability and proliferation of hematopoietic progenitor cells. This can be done using chemical agents known in the art, such as adriamycin, cytosine arabinoside, vincristine, cyclophosphamide, busulfan, prednisone, and M-AMSA (Amascrine). Purging can also be accomplished with tumor specific antibodies. Many such antibodies are known in the art. Alternatively, chemotherapeutic agents or anti-tumor antibodies can be administered directly to the mammal which is receiving bryostatin. Bryostatin may enhance the antineoplastic activity of the chemotherapeutic agent or antibody. Alternatively, use of bryostatin should allow higher amounts of the antineoplastic agent to be used, because of a reduction in the deleterious effects upon hematopoiesis.

The bryostatins may be used to counteract the effects of many types of diseases. For example, anemias in which erythroid cell populations are low often require transfusions. Use of bryostatins to stimulate erythroid cell formation could prevent the need for transfusions. Such anemias include anemia of chronic disease, congenital anemias, acquired aplastic anemia, acquired or congenital pancytopenia, and Fanconi's anemia. Similarly after or during prolonged chemotherapy, hematopoietic cells are often depleted. Thus, bryostatins could serve to bolster such cell populations. In addition, in patients who are compromised in their immune systems, either due to immunosuppressive drugs or immunosuppressive diseases, the bryostatins can be used to stimulate the patients' white cells to fight infections (by activation of neutrophils). Other situations where bryostatins can be advantageously used are in situations where populations of humans and other mammals have been exposed to radiation, such as from nuclear weapons or from environmental leakage from nuclear power stations. In those cases, administration of bryostatins could relieve the deleterious and often fatal effects of radiation on hematopoietic cells.

The bryostatins can be administered by any means known in the art. Because the desired targets of the bryostatins occur primarily in the bone marrow and blood system it is desirable that the method of administration allows the bryostatins to reach those tissues. Bryostatins can be administered parenterally by injection, rapid infusion, nasopharyngeal adsorption, dermal adsorption, or orally. One preferred method of administration of bryostatins is continuous infusion. For example, an osmotic micropump can be implanted subcutaneously and bryostatin infused over a period of days. Generally between 10 and 1000 ug per kilogram per day is desirable to stimulate hematopoietic cells.

The following examples are meant to illustrate the foregoing invention and do not limit the invention, which is specifically defined by the claims appended below.

EXAMPLES

EXAMPLE 1

Figure 2:
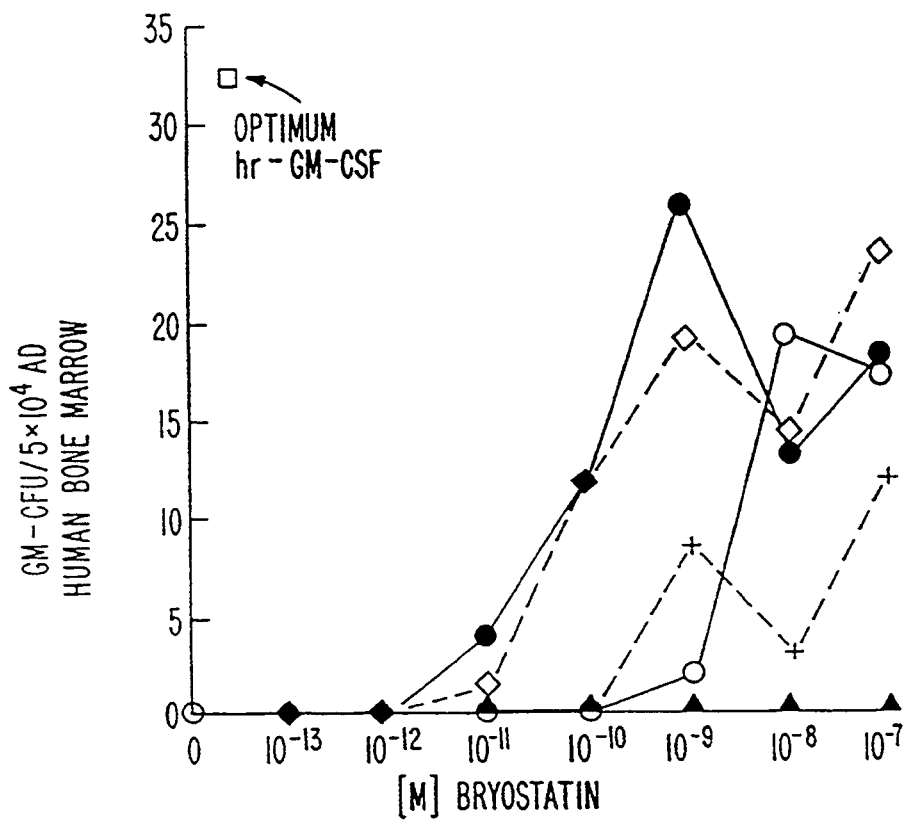
FIG. 2 shows the effect of bryostatins on granulocyte-macrophage colony growth in vitro.

This example demonstrates the stimulatory effect of bryostatins on granulocyte-macrophage colony formation. Granulocyte-macrophage colony-forming unit (CFU-GM) colonies were enumerated from light-density, adherence-depleted normal human bone marrow cells. Cells were suspended in supplemented McCoy's 5A medium containing 0.3% agar and plated in 35-mm Petri dishes as described in Pike et al, J. Cell Physiol., vol. 76, pp. 77–83, 1970. Results are shown in FIG. 2. Colonies were enumerated following incubation of bone marrow with cells with rHGM-CSF at 50 mg/ml (Genetrics Institute) or bryostatin 1 (●) bryostatin 3(o), bryostatin 8(◆), bryostatin 9(+), or bryostatin 13 (▲)at the concentrations indicated. After 14 days of culture at 37° C. in a humidified atmosphere containing 7.5% $CO_2$, colonies of greater or equal to 50 cells were scored. Representative results from one of several experiments are reported as the mean colony number from quadruplicate samples. SEM is within 10% of the means number.

Bryostatins 1, 3, 8, and 9 were found to mediate a dose-dependent stimulation of CFU-GM with the maximal effective concentration between 1 and 100 nM. Colony stimulating activity was observed with a concentration as low as 0.01 nM for bryostatins 1 and 8, which are the most potent of the four active congeners tested. While the amplitude of granulocyte-macrophage colony response was similar for bryostatin 3 at the higher concentrations (i.e., 10–100 nM), this agent was clearly less potent than bryostatin 1 to 8. Bryostatin 9 was only a weak stimulator of normal colony growth, whereas bryostatin 13 was completely inactive.

Analysis of colony morphology revealed that bryostatin 1, like rHGM-CSF, stimulated primarily mixed granulocyte-macrophage and pure granulocyte colonies at 7 and 14 days of culture.

EXAMPLE 2

This example shows that bryostatin 1 exerts its effect directly on cells.

Figure 3:
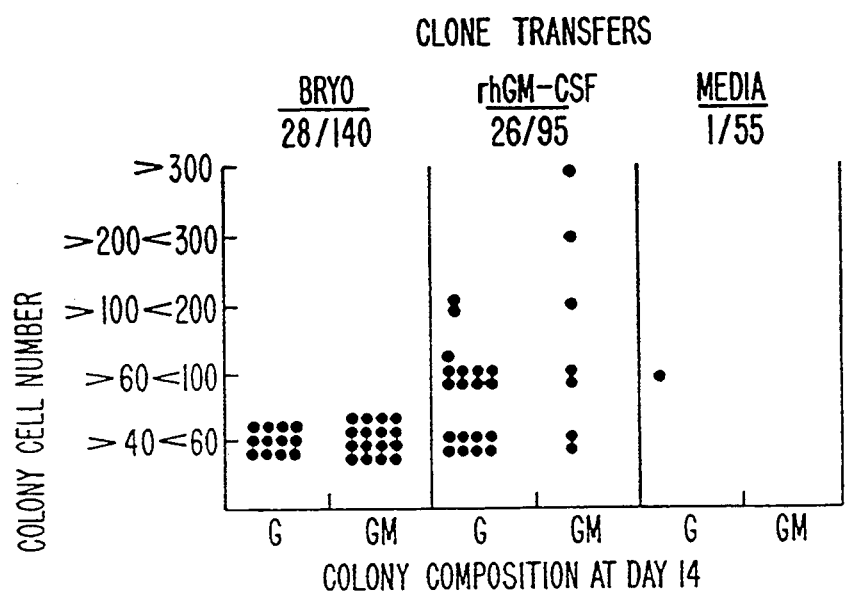
FIG. 3 shows the effect of bryostatin 1 on the growth of transferred clones. Clones were initially grown in the presence of bryostatin 1, and transferred to media containing either bryostatin 1, recombinant human GM-CSF, or media alone.

Assays were performed essentially as described in Metcalf et al, Blood, vol. 67, pp. 37–45, 1986. Briefly, cultures of normal human bone marrow were initiated in medium containing 10 nM bryostatin 1. Following 4 days of growth, clones of 4–8 cells were carefully removed using a glass pipette to avoid contamination by surrounding cells and transferred to secondary plates containing either rhGM-CSF (50 ng/ml) or bryostatin 1 (10 nM) as the source of CSF). After an additional 10 days of culture, the number of clones that had proliferated to form a colony of 40 cells or more was determined. Further growth was not observed in colonies transferred to plates containing no added CSF. (See FIG. 3.)

Each symbol (●) represents a colony. Its height in each column is proportional to the number of cells in that colony. The data directly above sections G of the column represent colonies composed entirely of granulocytic cells. The data above sections GM in the column represent colonies composed of both granulocytic and monocytic cells. No colonies in secondary plates were detected that were composed of macrophage-monocyte cells only. The numerator in the fraction at the top of each column represents the number of colonies that developed in the secondary plate, and the denominator represents the total number of clones transferred. The clones from primary plates initiated with bryostatin produced full-size colonies only on the secondary plates to which bryostatin or rhGM-CSF had been added. This indicates that the stimulatory effect of bryostatin 1 and rhGM-CSF is exerted directly.

Further, an attempt to produce a conditioned medium from bone marrow cells in the presence of bryostatin was unsuccessful. Nonadherence-depleted human bone marrow, which was composed of a mixture of progenitor plus ancillary cells, was incubated in culture medium that contained a maximal stimulatory concentration of bryostatin (i.e. 1–10 nM) for 5 days. The supernatant was aspirated and tested for the presences of a GM-CSF after fractionation by passage over a Sephadex G-25 gel filtration column to remove the bryostatin (i.e., $M_r$, 884). The resulting void volume, which contains the large molecular weight polypeptide growth factors, was evaluated for CSF activity. This supernatant was tested at both 10% (vol/vol) final concentrations in the culture plates and failed to stimulate GM-CFU growth.

EXAMPLE 3

This example demonstrates the stimulatory effect of bryostatin 1 on human erythrocyte progenitors.

Figure 4:
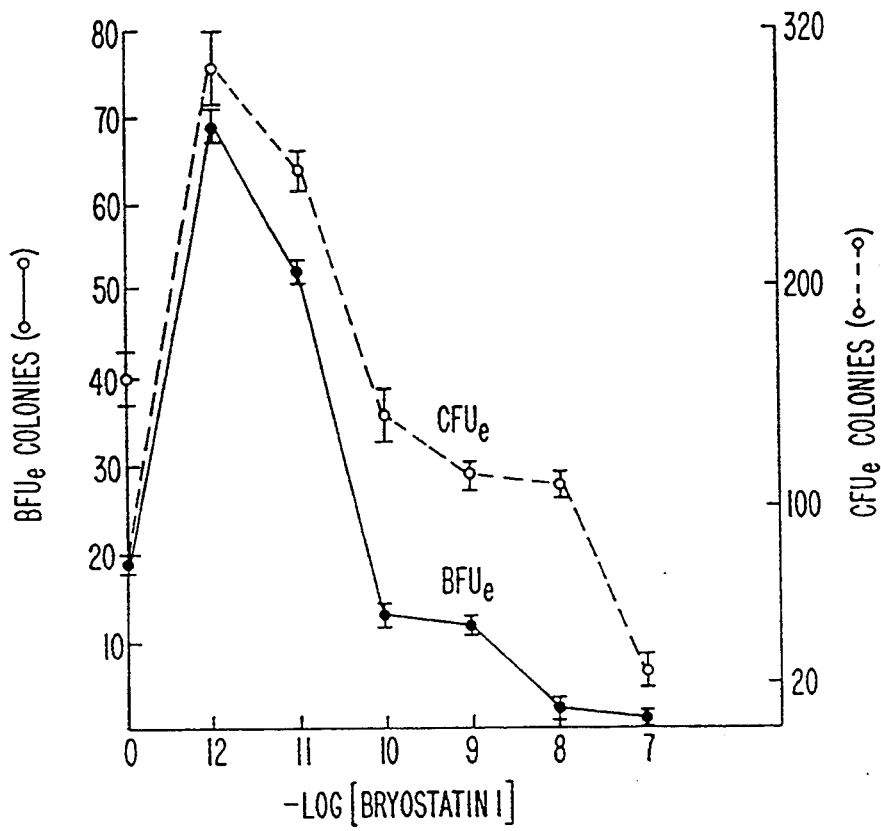
FIG. 4 depicts the effect of bryostatin 1 on growth of human erythroid progenitors.

Assays for both early (BFU-E) and late (CFU-E) progenitors were enumerated as described in McLeod et al, Blood, vol. 44, p. 517 (1974) using the plasma-clot method and optimal concentrations of erythropoietin. Bryostatin 1 stimulated both early BFU-E and late CFU-E human erythroid progenitors growth in plasma clots. See FIG. 4. The maximal stimulatory concentration was between 1 and 10 pM, with an inhibitory effect noted at concentrations above 1 nM.

EXAMPLE 4

This example demonstrates that bryostatin 1 but not 13 causes neutrophils to chemiluminesce in the presence of luminol. In addition neutrophils are shown to be activated to kill K562 target cells by bryostatin 1.

Normal human peripheral blood neutrophils were highly purified on a double Ficoll density gradient and suspended in Dulbecco's phosphate-buffered saline supplemented with $Ca^{2+}$ and $Mg^{2+}$. First, substances to be tested were incubated with the neutrophils for 15 min. At this point 10 uM luminol (5-amino-2, 3-dihydro-1,4-phtyalazinedione) was added to each sample. The generation of chemiluminescence was measured in a luminometer at 1.25 min intervals for up to 20 min.

Figure 5:
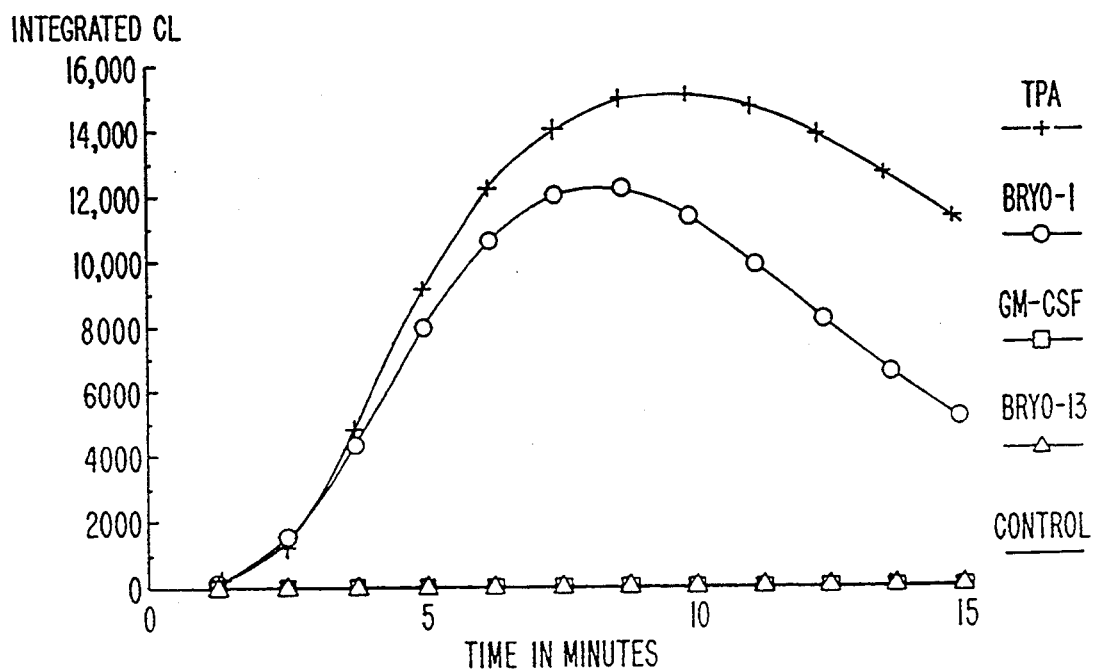
FIG. 5 shows the generation of chemiluminscence by neutrophils incubated with bryostatins 1 and 13, as well as recombinant human GM-CSF, and phorbol 12-myristate 13-acetate (TPA).

Bryostatin 1, but not bryostatin 13, was found to be a potent activator of neutrophil chemiluminescence, a measure of oxide radical formation. Activation follows a similar time course to that for the known activator phorbol 12-myristate 13-acetate. See FIG. 5. TPA was at 150 nM and recombinant human GM-CSF at 50 ng/ml.

Furthermore, activation of neutrophil cytotoxicity, as measured by killing of $^{51}Cr$-labeled K562 tumor target cells was also sitmulated by bryostatin 1 (Table 1). Neutrophils were purified as described above. Neutrophils were incubated at a density of $3 \times 10^6$ cells per ml first with various concentrations of bryostatin 1 (0.1 uM to 0.1 nM), rhGM-CSF (50 ng/ml), or in medium alone for 2 hr. Following two washes, the cells were added to the $^{51}Cr$-labeled K562 target cells at effector/target cell ratios of 30:1, 15:1, or 7.5:1 as indicated. Control plates containing $^{51}Cr$-labeled K562 cells and either bryostatin or medium alone were evaluated to determine the spontaneous release of isotope. The plates containing the cells were centrifuged at 250 $\times$g for 2 min and then incubated for 3 hrs at 37+ C. One hundred microliters of the supernatant was harvested from each well, and the amount of radioactivity present was determined in a gamma scintillation counter. The maximum release of $^{51}Cr$ was determined by assaying supernatant obtained from wells in which the cells were completely lysed with 6 M HCl.

Neutrophil activation was maximal between 10 and 100 nM bryostatin 1, a concentration range that can promote myeloid hematopoietic growth. Whereas rhGM-CSF has been reported to activate eosinophils and neutrophils we were unable to detect either the induction of chemiluminescence or of cytotoxicity in neutrophils when rhGM-CSF at 50 ng/ml, a maximal-stimulatory concentration for granulocyte-macrophage-colony formation.

EXAMPLE 5

This example demonstrates that bryostatin 1 is not toxic to a mammal and stimulates multipotential hematopoietic progenitors in vivo.

Using osmotic micropumps (Alzet) implanted subcutaneously in 6 week old female $BDF_1$ mice, bryostatin infused for 7 days had no major organ toxic effects at any of the doses employed. A dose-response stimulatory effect on multi-potential hematopoietic progenitors was noted. The administration of 144 ug/kg/d (max. dose) increased CFU-S, CFU-GM and BFU-E compared to control animals infused with vehicle alone. CFU-S from spleen cells of treated animals were increased 2-fold (19 vs. 39 colonies per $10^6$ cells injected), while bone marrow CFU-S was not altered. Likewise, CFU-GM colonies from spleen cells were increased 3.6-fold (52 vs. 188 per $10^6$ cells injected), and increased 2-fold (73 vs. 150 per $10^5$ nuc. cells) in bone marrow. Erythroid BFU-E colonies from spleen cells also demonstrated a 2-fold increase (28 vs. 58 per $10^6$ cells), while no change in bone marrow BFU-E progenitors was found. The increment in progenitor cells was not accompanied by a significant change in the differential peripheral white blood cell, hemocrit, bone marrow cellularity or spleen weights.

The results demonstrate the continuous infusion of bryostatin is non-toxic and can stimulate effectively murine multi-potential hematopoietic progenitor cells in vivo. The stimulatory effect of bryo is similar to its effect on multipotential progenitor cells in vitro and mimics the reported effect of infusion of rIL-3 and rGM-CSF.

TABLE 1

| Activated neutrophil cytotoxicity for K562 target cells | | | |
|---|---|---|---|
| | % specific lysis at effector/target ratio | | |
| Addition | 30 | 15 | 7.5 |
| Neutrophils Plus Bryostatin 1 | | | |
| $10^{-7}$ M | 102.8 | 18.1 | 7.8 |
| $10^{-8}$ M | 8.4 | 2.4 | 0 |
| $10^{-9}$ M | 0.9 | 1.8 | 0 |
| $10^{-10}$ M | −0.8 | 1.0 | 0.9 |
| Medium alone | 0.9 | 1.0 | −0.8 |
| rHGM-CSF (50 ng/ml) | 1.6 | 0.9 | −0.7 |
| Bryostatin alone | | | |
| $10^{-7}$ M | 1.5 | 0.3 | −0.6 |
| $10^{-8}$ M | 0.9 | 1.0 | 0.3 |

Assessment of neutrophil cytotoxicity induced by bryostatin 1. K562 cells were labeled with $Na^{51}Cr_2O_4$ and adjusted to a concentration of $10^3$ cells per ml in RPMI 1640 medium. Activated neutrophil cytotoxicity was determined. The results are expressed as the percentage of specific isotope released at the indicated effector/target cell ratio calculated as follows: % specific lysis = [(mean cpm of sample − means cpm spontaneously released/(mean cpm maximal − mean cpm spontaneously released)] × 100. Maximum induced cpm released as 7364±149. The maximum means % specific lysis from triplicate determinations from a representative experiment is shown.

We claim:

1. A method of stimulating the formation of CFU-GM comprising:
   obtaining a cell preparation containing hematopoietic stem cells; and
   incubating the cell preparation in vitro with a bryostatin having an acylated C20 carbon in an amount effective to stimulate the formation of granulocyte-macrophage colonies.

2. The method of claim 1 wherein the cell population is obtained from bone marrow.

3. The method of claim 1 wherein the cell population is obtained from peripheral blood cells.

4. The method of claim 1 wherein the effective amount of bryostatin is a concentration of from about $10^{-12}M$ to about $10^{-7}M$.

5. The method of claim 4 wherein the concentration of bryostatin is about $10^{-9}M$ to about $10^{-7}M$.

6. The method of claim 1 wherein a chemotherapeutic agent is also added to the cell preparation in an amount effective to kill malignant cells.

7. The method of claim 6 wherein the chemotherapeutic agent is bryostatin 13.

8. The method of claim 6 wherein the chemotherapeutic agent is selected from the group consisting of: adriamycin, cytosine arabanoside, vincristine, cyclophosphamide, busulfan, prednisone, and M-AMSA.

9. The method of claim 1 wherein a monoclonal antibody is used to remove said malignant cells from the cell preparation.

10. The method of claim 1 wherein the cell preparation, after incubation with bryostatin, is administered to a mammal.

11. The method of claim 1 wherein the bryostatin is selected from the group consisting of 1, 3, 8, and 9.

12. The method of claim 1 wherein the cell preparation is treated with ionizing radiation in an amount effective to kill malignant cells.

13. A method of increasing formation of CFU-GM and BFU-E in a mammal comprising:
    administering a bryostatin having an acylated C20 carbon to the mammal in an amount effective to increase the and formation of CFU-GM or BFU-E.

14. The method of claim 12, comprising:
    administering bryostain 13 to the mammal in an amount effective to arrest the growth of a tumor; and
    administering bryostatin 1 to the mammal in an amount effective to stimulate formation of CFU-GM and BFU-E.

15. The method of claim 13 wherein the bryostatin is administered by continuous infusion.

16. The method of claim 13 wherein the bryostatin is administered subcutaneously.

17. The method of claim 13 wherein the bryostatin is selected from the group consisting of 1, 3, 8, and 9.

18. A method of stimulating the formation of CFU-E and BFU-E comprising:
    obtaining a cell preparation containing hematopoietic stem and
    incubating the cell preparation in vitro with erythropoietin and a bryostatin having an acylated C20 carbon in an amount effective to increase the formation of CFU-E and BFU-E.

19. The method of claim 18 wherein the cell preparation is obtained from bone marrow.

20. The method of claim 18 wherein the cell preparation is obtained from peripheral blood cells.

21. The method of claim 18 wherein the concentration of bryostatin is about $10^{-10}M$ to about $10^{-12}M$.

22. The method of claim 18 wherein a chemotherapeutic agent is also added to the cell preparation in an amount effective to kill malignant cells.

23. The method of claim 22, wherein the chemotherapeutic agent is bryostatin 13.

24. The method of claim 24, wherein the chemotherapeutic agent is selected from the group consisting of: adriamycin, cytosine arabinoside, vincristine, cyclophosphamide, busulfan, prednisone, and M-AMSA.

25. The method of claim 18 wherein the cell preparation further contains malignant cells and a nonoclonal antibody is used to remove said malignant cells from the cell preparation.

26. The method of claim 18 wherein the cell preparation, after incubation with bryostatin, is administered to a mammal.

27. The method of claim 18 wherein the bryostatin is selected from the group consisting of 1, 3, 8, and 9.

28. The method of claim 18 wherein the cell preparation is treated with ionizing radiation in an amount effective to kill malignant cells.

* * * * *

UNITED STATES PATENT AND TRADEMARK OFFICE
CERTIFICATE OF CORRECTION

PATENT NO. : 5,358,711
DATED : October 25, 1994
INVENTOR(S) : W. Stratford May, et al.

It is certified that error appears in the above-identified patent and that said Letters Patent is hereby corrected as shown below:

Column 9, line 49,
    Claim 13, line 5, please delete the word "and" before "formation", and insert --and-- between "CFU-GM" and "BFU-E" in place of "or".

Column 10, line 1,
    At claim 14, change the dependency from "12" to "13".

Column 10, line 33,
    At claim 24, change the dependency from "24" to "18".

Signed and Sealed this

Nineteenth Day of September, 1995

Attest:

BRUCE LEHMAN

Attesting Officer     Commissioner of Patents and Trademarks